United States Patent [19]

Travers et al.

[11] Patent Number: 5,659,104
[45] Date of Patent: Aug. 19, 1997

[54] OLEFIN ISOMERISATION PROCESS

[75] Inventors: Christine Travers, Rueil-Malmaison; Jean-Pierre Burzynski, Sainte-Foy-les-Lyon; Albert Chaillard, Rueil-Malmaison, all of France

[73] Assignee: Institut Francais Du Petrole, Rueil-Malmaison, France

[21] Appl. No.: 537,924

[22] PCT Filed: Feb. 17, 1995

[86] PCT No.: PCT/FR95/00190

§ 371 Date: Jan. 22, 1996

§ 102(e) Date: Jan. 22, 1996

[87] PCT Pub. No.: WO95/23777

PCT Pub. Date: Sep. 8, 1995

[30] Foreign Application Priority Data

Mar. 1, 1994 [FR] France .................................. 94 02432

[51] Int. Cl.$^6$ .................................. C07C 5/22; C07C 5/27
[52] U.S. Cl. .................................................. 585/671
[58] Field of Search .................................................. 585/671

[56] References Cited

U.S. PATENT DOCUMENTS 2,301,342  11/1942  Sumerford et al. .
2,422,884   6/1947  Burgin ............................ 585/671
5,321,195   6/1994  Travers et al. ................... 585/671

FOREIGN PATENT DOCUMENTS 0 588 680   3/1994  European Pat. Off. .
59-123538   7/1984  Japan .
1028168     5/1966  United Kingdom .
1065008     4/1967  United Kingdom .

*Primary Examiner*—Glenn A. Caldalola
*Assistant Examiner*—Elizabeth D. Wood
*Attorney, Agent, or Firm*—Millen, White, Zelano, & Branigan, P.C.

[57] ABSTRACT

The invention concerns an isomerisation process for n-olefins containing at most 20 carbon atoms, consisting of bringing a feed containing the olefins into contact with an alumina based catalyst impregnated with 0.03% to 0.6% by weight of titanium and 0.05% to 5% by weight of an oxide of an element from group IIIA. The process can then be carried out in the presence of a small quantity of steam or it can be carried out in the absence of steam.

24 Claims, No Drawings

OLEFIN ISOMERISATION PROCESS

PRIOR ART

The present invention concerns a skeletal isomerisation process for olefins containing at most 20 carbon atoms, more particularly the isomerisation of n-butenes to isobutenes and n-pentenes to isopentenes (isoamylenes), using a particular catalyst.

Reducing the amount of alkyl lead in petrol has meant that for a number of years, the refiner has had to incorporate different compounds into petrols, in particular alcohols and esters, to increase the octane number. In addition to methanol which is one of the most widely known additives, MTBE (methyl tertiobutyl ether) has anti-knock properties which improve the quality of petrols and increase their octane index to a greater extent than that obtained using methanol. MTBE also has other advantages, such as:

- a boiling point which is similar to that of the petrol components with the poorest anti-knock properties;
- a vapour tension which is compatible with the above components;
- an excellent pour-point;
- low solubility in water;
- complete miscibility in hydrocarbons, etc.

MTBE is normally obtained from isobutene and methanol in accordance with the following reaction:

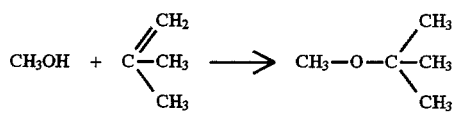

The isobutene is generally contained in $C_3$–$C_4$ olefinic cuts from catalytic cracking, steam cracking, thermal cracking and visbreaking effluents. The quantities of isobutene provided by these processes, however, are not sufficient to allow widespread development of the MTBE production process.

For this reason, complete or almost complete isomerisation of the butenes contained in the effluents from the processes described above has been proposed in order to produce larger quantities of isobutenes.

A number of processes have been described in the literature, using a variety of catalysts. The catalysts used are generally alumina based, or more particularly activated or steam treated aluminas (U.S. Pat No. 3,558,733), using eta or gamma alumina, halogenated aluminas (U.S. Pat. No. 2,417,647), bauxite, aluminas treated with boron derivatives (U.S. Pat. No. 3,558,733), silicon (U.S. Pat. No. 4,013,590, U.S. Pat. No. 4,038,337, GB-A 2 129 701 and U.S. Pat. No. 4,434,315), group IIIA elements or zirconium and various aluminosilicates, etc.

The majority of these catalysts exhibit fairly low conversions per pass and low selectivity due to side reactions such as cracking or polymerisation. These latter reactions also cause a rapid decrease in performance and thus poor performance stability over time.

AIM OF THE INVENTION

In our recent patent (FR-92/10.949), we discovered that a catalyst obtained from alumina, preferably eta or gamma alumina, to which a specific quantity of titanium (0.03% to 0.6% by weight) had been added and which was preferably steam treated under precise conditions, surprisingly produced substantially improved selectivities, conversions and cycle times if the catalyst was used in the presence of steam.

The present invention consists in using a modified catalyst compared to that described in FR-92/10.949, which increases the isobutene yield and above all considerably improves stability, and which can be used to carry out the skeletal isomerisation of n-pentenes or n-butenes with a low or zero quantity of water.

The catalyst is obtained from alumina, preferably eta or gamma alumina, to which 0.03% to 0.6% by weight of titanium and 0.05% to 5% by weight of an oxide of an element from group IIIA (boron, aluminium, gallium, indium, thallium) has been added, this element preferably being boron. This catalyst can then preferably be steam treated under specific conditions.

DETAILED DESCRIPTION

In the process of the invention, either a $C_4$ olefinic cut alone produced from the processes described above can be isomerised after removal of the $C_3$ cut, or the whole $C_3$–$C_4$ olefinic cut can be isomerised.

In accordance with the invention, linear olefinic hydrocarbons containing 5 to 20 carbon atoms per molecule can also be isomerised.

The feed to be isomerised is brought into contact with the catalyst at a temperature of between 300° C. and 570° C. (preferably between 310° C. and 550° C. when it is constituted by butenes and/or pentenes) at a pressure of between 1 and 10 bars absolute (preferably between 1 and 5 bars absolute when the feed is constituted by butenes and/or pentenes).

The space velocity is between 0.1 and 10 $h^{-1}$ expressed as the volume of olefinic feed per volume of catalyst per hour (preferably between 0.5 and 6 $h^{-1}$ when the feed is constituted by butenes and/or pentenes).

In accordance with the invention, since secondary reactions responsible for coking are considerably reduced, the process can be carried out in the presence of very low quantities of water, or even in the absence of water. The quantity of water injected into the reactor is such that the molar ratio of $H_2O$ olefinic hydrocarbons is between 0 and 0.3, preferably between 0.05 and 0.25 when the feed is constituted by butenes and/or pentenes.

Commercial aluminas, preferably activated aluminas, can be used to prepare the catalyst, preferably selected from the group formed by eta and gamma aluminas, and with a low alkali metal content, for example containing less than 0.1% of sodium.

The specific surface area of the alumina is advantageously between 10 and 500 $m^2/g$, preferably between 50 and 450 $m^2/g$, the pore volume being between 0.4 and 0.8 $cm^3/g$.

The catalysts of the invention are prepared by adding 0.05% to 1%, preferably 0.085% to 0.5%, of titanium dioxide to the alumina support. Any suitable method of adding the titanium dioxide can be used. A titanium compound may, for example, be dissolved in the solution containing the aluminium compound and the precipitation conditions for the alumina can be adjusted so that titanium hydroxide coprecipitates. In addition, at least one titanium compound selected from the group formed by titanium dioxide in the form of rutile and octahedrite, sub-oxides of TiO and $Ti_2O_3$, titanic acids, alkaline, alkaline-earth and ammonium titanates and soluble and insoluble organic and inorganic titanium salts can be added to hydrated alumina in the form of a gel ($\alpha$-trihydrate or $\beta$-trihydrate, or aluminium $\alpha$-monohydrate).

It can also be prepared from an alumina support which is formed and impregnated with a solution of an organic or inorganic titanium salt; in general, the titanium can be introduced before, during or after the catalyst support is formed.

A preferred process consists in adding at least one organic titanium compound, for example tetraethoxytitanium, to an organic solution (for example alcoholic) of at least one organic aluminium compound (for example an alkoxyaluminium such as aluminium isopropylate), and hydrolysing the solution obtained.

The titanium can also be added in the form of a readily hydrolysable inorganic compound such as titanium tetrachloride, $TiCl_4$.

In another preferred process, specific quantities of a titanium based organic compound, for example an alkoxytitanium such as tetraethyltitanium and/or an inorganic titanium compound (for example titanium trichloride) are added during the ZIEGLER synthesis of polyalkoxyaluminium, by reaction of an alkylaluminium (for example triethylaluminium), ethylene, and at least one of the above titanium compounds. The polyalkoxyaluminium is prepared by polymerisation followed by oxidation, and hydrolysis produces polyols and the titanium-containing hydrated alumina.

It has been shown experimentally that these processes produce a particularly high dispersion of titanium ions in the alumina matrix, obtained after hydrolysis of the alkoxyaluminium or polyalkoxyaluminium. When, for example, the support is in the form of spherules or extrudates, etc.., the preferred titanium impregnation processes can produce a $TiO_2$ concentration which is constant between one spherule and another; if the average desired concentration is $C\%$, the concentration $C$ from one spherule to another or from one extrudate to another is between $C\pm5\%$ of this concentration and even between $\pm3\%$ by weight using the preferred methods of the invention. More particularly, further improved results have been obtained using catalyst supports containing 0.06% to 0.15% of $TiO_2$.

The oxide of the group IIIA element can be deposited either before or after titanium deposition. Deposition can be carried out by impregnation using an excess of solution in an acidic solution of the selected group IIIA element. It can also be carried out by capillary diffusion impregnation, or dry impregnation, into the pore volume of the support. In the case of boron, orthoboric acid or any sufficiently soluble boron compound can be used.

The catalyst obtained is then dried at a temperature of between 100° C. and 130° C. and optionally calcined in air at a temperature of between 400° C. and 800° C., preferably between 450° C. and 750° C., for periods of between 1 and 5 hours. It can then advantageously be steam treated at a temperature of between 120° C. and 700° C., preferably between 300° C. and 700° C., at a partial pressure of steam of more than 0.5 bar, preferably between 0.6 and 1 bar, for a period of 0.5 to 120 hours, preferably 1 to 100 hours.

The titanium and group IIIA element concentrations were measured using X ray fluorescence.

Isomerisation performances are expressed as follows:
1. Butene conversion:

$$C = \frac{\Sigma(\% \text{ n-butenes})\text{feed} - \Sigma(\% \text{ n-butenes})\text{effluent}}{\Sigma(\% \text{ n-butenes})\text{feed}} \times 100$$

2. Isobutene selectivity:

$$S = \frac{(\% \text{ isobutenes})\text{effluent} - (\% \text{ isobutenes})\text{feed}}{\Sigma(\% \text{ n-butenes})\text{feed} - \Sigma(\% \text{ n-butenes})\text{effluent}} \times 100$$

3. Isobutene yield:

$R = C \times S / 100$

The following examples illustrate the invention without limiting its scope.

TABLE 1

| | | | |
|---|---|---|---|
| Temperature (°C.) | 450 | 450 | 470 |
| $H_2O/C_4^=$ mole | 0 | 0 | 0.2 |
| LHSV (h$^{-1}$) | 1 | 1 | 1 |
| Operating time (h) | 1 | 1 | 1 |

| | Feed | Catalyst A | Catalyst B | Catalyst B |
|---|---|---|---|---|
| $CH_4$ | | 0.06 | 0.06 | 0.05 |
| $C_2$ | | 0.02 | 0.02 | 0.02 |
| $C_2^=$ | | 0.15 | 0.12 | 0.09 |
| $C_3$ | | 0.02 | 0.02 | 0.02 |
| $C_3^=$ | | 1.7 | 1.2 | 1.05 |
| $iC_4$ | 6.65 | 7.55 | 6.3 | 5.9 |
| $nC_4$ | 20.15 | 21.1 | 22.2 | 22.0 |
| $C_4^=2TR$ | 23.7 | 17.35 | 17.43 | 18.17 |
| $C_4^=1$ | 32.85 | 12.1 | 11.95 | 11.8 |
| $iC_4^=$ | 1.3 | 22.4 | 23.90 | 24.0 |
| $C_4^=2Cis$ | 15.15 | 13.15 | 13.15 | 13.4 |
| $C_4^=$ | 0 | 0 | 0 | 0 |
| $C_5^+$ | 0.2 | 4.4 | 3.65 | 3.5 |
| Conversion % | | 40.6 | 40.7 | 39.5 |
| Selectivity % | | 72.7 | 77.4 | 80.1 |
| Yield % | | 29.5 | 31.5 | 31.65 |

In Table 1, $C_2$ designates ethane; $C_2^=$: ethylene; $C_3$: propane; $iC_4$: isobutane; $nC_4$: n-butane; $C_4^=2TR$: trans 2-butene; $C_4^=1$: 1-butene; $iC_4^=$: isobutene; $C_4^=2Cis$: cis 2-butene; $C_4^{==}$: butadiene; and $C_5^+$: hydrocarbons containing at least 5 carbon atoms.

TABLE 2

| | Catalyst A | Catalyst B | Catalyst B |
|---|---|---|---|
| $H_2O/C_4^=$ (mole) | 0 | 0 | 0.2 |
| LHSV (h$^{-1}$) | 1 | 1 | 1 |
| Temperature (°C.) | 450 | 450 | 470 |
| Operating time (h) | 18 | 18 | 18 |
| Conversion (%) | 36.9 | 39.8 | 39.35 |
| Selectivity (%) | 73.4 | 77.9 | 80.3 |
| Yield (%) | 27.1 | 31.0 | 31.6 |

EXAMPLE 1

Catalyst A not in accordance with the invention

A commercial γ alumina with a surface area of 200 m$^2$/g was impregnated with 0.1% of titanium from titanium oxalate decahydrate in aqueous solution, then dried at 100° C. for two hours and calcined at 600° C. for two hours. Catalyst A obtained was treated with steam at 560° C. for 20 hours at a partial pressure of steam of 0.8 bar. The catalyst was used to isomerise a $C_4$ olefinic cut with the composition shown in Table 1. The operating conditions were as follows:

| LHSV = | 1 h⁻¹ |
|---|---|
| $H_2O/C_4^=$ (mole) = | 0 |
| T = | 450° C. |
| p = | 1 bar absolute |

The performances obtained after 1 hour of operation are shown in Table 1 and those after 30 hours of operation are shown in Table 2.

EXAMPLE 2

Catalyst B in accordance with the invention 1.2% by weight of boron from boric acid was deposited on catalyst A prepared as in Example 1 by dry impregnating into the pore volume. The product obtained was dried at 100° C. for 2 hours, then calcined at 600° C. for 2 hours. Catalyst B thus obtained was treated in steam at 560° C. for 20 hours with a partial pressure of steam of 0.8 bar. This catalyst was used under the same conditions as those described in Example 1. The performances obtained after 1 hour of operation are shown in Table 1 and those after 30 hours of operation are shown in Table 2.

The performances of catalyst B were better, in particular in terms of yield and stability, compared with those of catalyst A.

EXAMPLE 3 in accordance with the invention

Catalyst B prepared as described in Example 2 was used to isomerise a $C_4$ olefinic cut under different conditions to those of Example 2, i.e., with a small amount of water. The operating conditions were as follows:

| LHSV = | 1 h⁻¹ |
|---|---|
| $H_2O/C_4^=$ (mole) = | 0.2 |
| T = | 470° C. |
| p = | 1 bar absolute |

The performances obtained after 1 hour of operation are shown in Table 1 and those after 30 hours of operation are shown in Table 2. Again, the performances in terms of yield and stability under these conditions were considerably better than those of catalyst A.

We claim:

1. A skeletal isomerisation process for linear olefinic hydrocarbons containing at most 20 carbon atoms per molecule, characterised in that said hydrocarbons are brought into contact with a catalyst containing alumina, 0.03% to 0.6% by weight of titanium and 0.05% to 5% by weight of an oxide of an element from group IIIA, at a temperature of between 300° C. and 570° C., a pressure of between 1 and 10 bars, and a space velocity of between 0.1 and 10 h⁻¹.

2. A process according to claim 1, wherein the element from group IIIA is boron.

3. A process according to claim 1 or characterised in that the process takes place in the presence of an injection of water such that the molar ratio of $H_2O$/olefinic hydrocarbons is at most 0.3.

4. A process according to claim 1, characterised in that the catalyst undergoes steam treatment before being brought into contact with the hydrocarbons, said treatment taking place at between 120° C. and 700° C. and at a partial pressure of steam of more than 0.5 bar for a period of 0.5 to 120 h.

5. A process according to claim 1, characterised in that the linear olefinic hydrocarbons treated are selected from the group formed by butenes and pentenes.

6. A process according to claim 1, characterised in that the isomerisation temperature is between 310° C. and 550° C.

7. A process according to claims 6, characterised in that the isomerisation pressure is between 1 and 5 bars.

8. A process according to claim 7, characterised in that the space velocity is between 0.5 and 6 h⁻¹.

9. A process according to claim 8, characterised in that the molar ratio of injected water/hydrocarbons is between 0.05 and 0.25.

10. A process according to claim 1, characterised in that the alumina is a gamma alumina.

11. A process according to claim 1, characterised in that the alumina is an eta alumina.

12. A process according to claim 1, characterised in that the sodium concentration in the alumina is less than 0.1% by weight.

13. A process according to claim 1, characterised in that the specific surface area of the alumina is between 10 and 550 m²/g.

14. A process according to claim 1, characterised in that the pore volume of the alumina is between 0.4 and 0.8 cm³/g.

15. A process according to claim 3, wherein the element from group IIIA is boron.

16. A process according to claim 4, wherein the element from group IIIA is boron.

17. A process according to claim 5, wherein the element from group IIIA is boron.

18. A process according to claim 9, wherein the element from group IIIA is boron.

19. A process according to claim 10, wherein the element from group IIIA is boron.

20. A process according to claim 11, wherein the element from group IIIA is boron.

21. A skeletal isomerisation process for linear olefinic hydrocarbons containing 4 carbon atoms per molecule, wherein said hydrocarbons are brought into contact with a catalyst containing alumina, 0.03% to 0.6% by weight of titanium and 0.05% to 5% by weight of an oxide of an element from group IIIA, at a temperature between 300° C. and 570° C., a pressure of between 1 and 10 bars, and a space velocity of between 0.1 and 10 h⁻¹, in the presence of an injection of water such that the molar ratio of $H_2O$/olefinic hydrocarbons is at most 0.3.

22. A process according to claim 1, wherein the process takes place in the absence of water such that the molar ratio of $H_2O$/olefinic hydrocarbon is 0.

23. A process according to claim 22, wherein the linear olefinic hydrocarbons treated are selected from the group formed by pentenes.

24. A process according to claim 5, wherein the process takes place in the absence of water such that the molar ratio of $H_2O$/olefinic hydrocarbon is 0.

* * * * *